(12) United States Patent
Hirono et al.

(10) Patent No.: US 6,937,940 B2
(45) Date of Patent: Aug. 30, 2005

(54) METHOD OF SUPERPOSING MOLECULAR STRUCTURES OF COMPOUNDS

(75) Inventors: Shuichi Hirono, Tokyo (JP); Kazuhiko Iwase, Saitama (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 108 days.

(21) Appl. No.: 10/297,598

(22) PCT Filed: Jun. 13, 2001

(86) PCT No.: PCT/JP01/04988

§ 371 (c)(1),
(2), (4) Date: Dec. 13, 2002

(87) PCT Pub. No.: WO01/97094

PCT Pub. Date: Dec. 20, 2001

(65) Prior Publication Data

US 2003/0149533 A1 Aug. 7, 2003

(30) Foreign Application Priority Data

Jun. 15, 2000 (JP) .................................... 2000-179769

(51) Int. Cl.[7] .............................................. G01N 31/00
(52) U.S. Cl. ............................ 702/27; 702/22; 702/30; 585/250; 585/400
(58) Field of Search ............................. 702/27, 22, 30, 702/19, 23, 13; 703/12; 585/400, 250

(56) References Cited

U.S. PATENT DOCUMENTS 6,070,127 A  5/2000  Hirono et al.

FOREIGN PATENT DOCUMENTS

JP  10-298113  11/1998

*Primary Examiner*—Bryan Bui
*Assistant Examiner*—Hien Vo
(74) *Attorney, Agent, or Firm*—Oblon, Spivak, McClelland, Maier & Neustadt, P.C.

(57) ABSTRACT

With compounds for drugs, agricultural chemicals, etc., the invention provides a novel method for superposing molecular structures of those compounds. A method for superposing molecular structures of compounds characterized in that, upon superposing the molecular structures of a plurality of compounds, (1) the characteristic groups (atoms) of compounds are roughly divided into four types of hydrophobicity (aliphatic chain/ring, aromatic ring and halogen), hydrogen-bonding donor, hydrogen-bonding acceptor and hydrogen-bonding donor/acceptor, (2) a molecule of compound with large radius of inertia calculated from constituting characteristic groups (atoms) is fixed, superposition is performed among a set of characteristic groups (atoms) with the same nature between two molecules of compounds, and operations of translation and rotation are performed in its neighborhood, (3) when causing the superposition of characteristic groups (atoms) between molecules of compounds by the operations of translation and rotation in (2), a score is given depending on the combination between respective characteristic groups (atoms), (4) scores of superposition are summed up, and (5) said operations of (2) through (4) are repeated to find out an orientation that acquires the highest score value.

21 Claims, 3 Drawing Sheets

Fig. 1

(a) Input of three-dimensional coordinates of molecule of compound and designation of characteristic groups (atoms)

↓ Hydrophobicity, hydrogen-bonding donor, hydrogen-bonding acceptor and hydrogen-bonding donor/acceptor.

(b) Translation of the gravity center of molecule of compound to the origin of coordinates.

↓

(c) Rotation ($0° \leq \phi, \psi < 360°, 0° \leq \theta \leq 180°$) of molecule of compound with small radius of inertia.

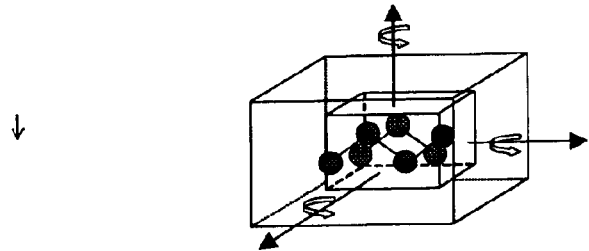

↓

(d) Translation (onto body-centered cubic lattice points or face-centered cubic lattice points of characteristic groups (atoms) of the counter molecule) of molecule of compound with small radius of inertia.

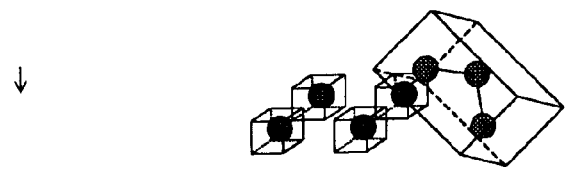

↓

(e) Determination of the best superposition.

↓ Criterion of evaluation (order of priority)
1) Highest score value, 2) Minimum value of rmsd (f) Optimization of the superposition by simplex method.

METHOD OF SUPERPOSING MOLECULAR STRUCTURES OF COMPOUNDS

BACKGROUND OF THE INVENTION

1. Technical Field

The present invention is a novel method (algorithm) for superposing the molecular structures of compounds for drugs, agricultural chemicals, etc., and it can be applied in the process of presuming active conformations from a number of metastable conformers. The invention is a novel superposing method (algorithm) for molecular structures of compounds utilizable for the presumption of active conformations on the compounds for drugs, agricultural chemicals, etc. and the creation of lead compounds for drugs, agricultural chemicals, etc. based on the three-dimensional structure data base searching.

2. Background Technologies

In the molecular designs of drugs, it is very important to determine the conformation of ligand molecule in the state of binding to proteins such as receptor and enzyme, that is, the active conformation thereof. For experimentally determining the active conformation of this ligand molecule, X-ray crystallography and NMR spectral analysis of the protein ligand complex have been known. However, it is accompanied with many difficulties that the crystallization of proteins such as receptor and enzyme is difficult, that enough quantity for analysis cannot be obtained, that molecular weight is too large to analyze, and the like. Hence, in computer assisted molecular designs, an approach is taken to presume the active conformation, based on the crystal structure of ligand molecule alone or the structure obtained from the calculation by molecular mechanics or molecular orbital method in a system that does not explicitly deal with the solvent molecules.

It has been considered that, even if the active conformation may not be the same as the most stable conformation obtained from the energy calculation, it comes to be a metastable conformation that is not so away, in view of energy. Moreover, it is also considered that the conformations of physiologically active peptide and some organic compounds in aqueous solution are close to the conformations in the state of binding to receptor and enzyme. In general, for the conformations of compounds binding to the same receptor and enzyme, a common feature that there is the same functional group in the same place in the three-dimensional space is considered, hence the superposition among functional groups of the metastable conformations is effective for the extraction of active conformation.

Based on this concept, the inventors provided a novel method for superposing molecular structures of compounds for drugs, agricultural chemicals, etc. in Japanese Unexamined Patent Publication No. Hei 10-298113. And, many inhibitor molecules in the state of binding to many enzymes were superposed, leading to the success in the reproduction of superposition obtained from X-ray crystallography. Furthermore, with respect to some inhibitor molecules, the inventors superposed among many metastable conformers and succeeded also in presuming the active conformations of inhibitor molecules in the state of binding to the enzyme (K. Iwase and S. Hirono, Journal of Computer-Aided Molecular Design, 13, 499-512, 1999). In the former, superpositions that cannot be presumed easily, such as superposition of elastase inhibitor TFK with TFA-Lys-Leu-ISO and superposition of 12 residues of OMTKY3 with Ace-Ala-Pro-Val-FPA were reproduced, and, in the latter, from superpositions of 113 conformers of NAPAP, 457 conformers of 4-TAPAP and 202 conformers of MQPA, the active conformations thereof were presumed, leading to the reconfirmation of the usefulness of superposing method provided in Japanese Unexamined Patent Publication No. Hei 10-298113. Here, the superposition obtained from X-ray crystallography means a superposition obtained by taking out inhibitor molecule's coordinates alone, after the least square fitting was performed among α carbon atoms on enzyme molecule's coordinates between enzyme-inhibitor complexes.

From the knowledge on structure-activity relationships and the like, many-compounds for drugs, agricultural chemicals, etc. having characteristic functional groups presumable to be concerned in the activity are known. In such cases, a superposing method that pays an attention to the characteristic functional groups common to compound molecules for drugs, agricultural chemicals, etc. is practical and necessary.

BRIEF SUMMARY OF THE INVENTION

Accordingly, the invention includes a method for superposing molecular structures of a plurality of compounds to derive a series of scores corresponding to different orientations and superpositions. Scoring may be assigned on likeness of characteristic groups compared to a fixed molecule.

BRIEF DESCRIPTION OF THE DRAWINGS

The invention will be explained in more detail hereinafter on the basis of drawings, which illustrate merely embodiments of the invention and are not intended to limit the claimed invention.

FIG. 1 shows the translation and rotation of the process and determination of best superposition.

DETAILED DESCRIPTION OF THE INVENTION

Figure 2:
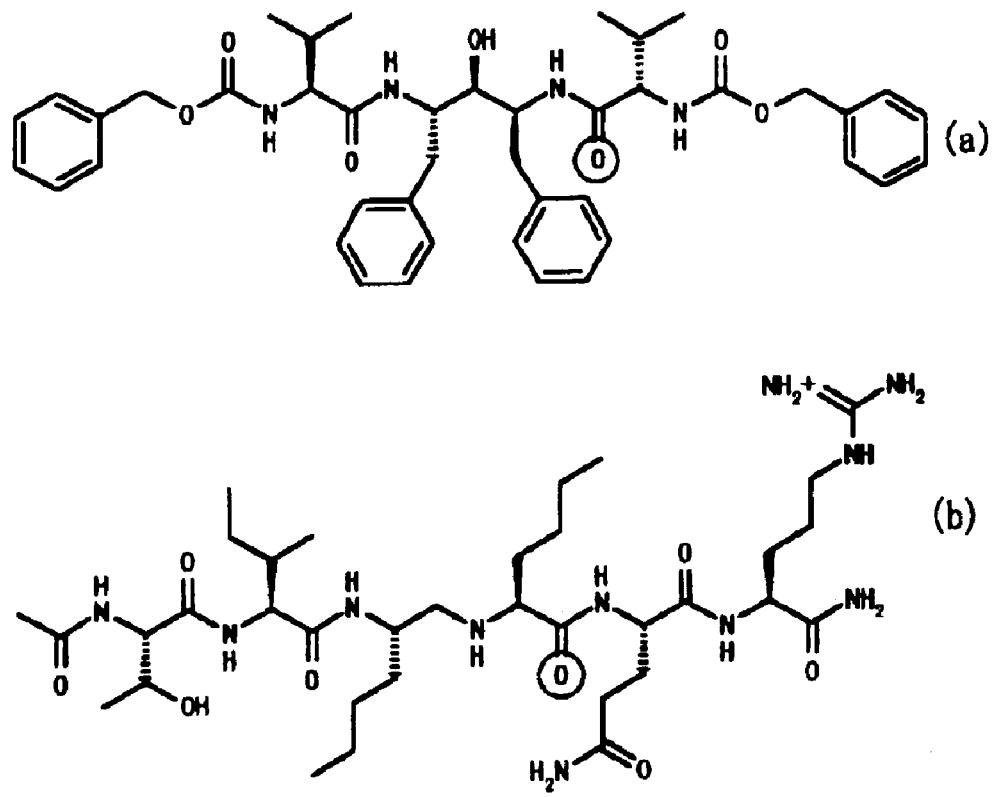
FIG. 2 shows the structural formula of different compounds.

As a result of diligent studies on the superposing method to solve the subject aforementioned, the inventors have found a new algorithm for superposing molecular structures of compounds, leading to the completion of the invention.

Namely, the invention provides a method for superposing the molecular structures of compounds characterized in that, upon superposing the molecular structures of a plurality of compounds, (1) the characteristic groups (atoms) of compounds are roughly divided into four types of hydrophobicity (aliphatic chain/ring, aromatic ring and halogen), hydrogen-bonding donor, hydrogen-bonding acceptor and hydrogen-bonding donor/acceptor, (2) a molecule of compound with large radius of inertia calculated from constituting characteristic groups (atoms) is fixed, superposition is performed among a set of characteristic groups (atoms) with the same nature between two molecules of compounds, and operations of translation and rotation are performed in its neighborhood, (3) when causing the superposition of characteristic groups (atoms) between molecules of compounds by the operations of translation and rotation in (2), a score is given depending on the combination between respective characteristic groups (atoms),
(4) scores of superposition are summed up, and
(5) said operations of (2) through (4) are repeated to find out an orientation that acquires the highest score value.

Moreover, when superposing the molecular structures of compounds for drugs, agricultural chemicals, etc. having characteristic functional groups presumable to be concerned in the activity, the invention provides a method of superposing the molecular structures of compounds characterized in that, given to every overlapping thereof. And, if characteristic groups (atoms) with the same nature are overlapped, then the score is added and, if characteristic groups (atoms) with different nature are overlapped, then the score is subtracted, but characteristic groups (atoms) having no overlapping are not made as a target of score (Table 1). However, the redundancy of overlapping with more than one pair between characteristic groups (atoms) with the same nature is not added. Thereafter, the scores are summed up on all the characteristic groups (atoms) that constitute the molecules.

TABLE 1

Score value between characteristic groups

| | Hydrophobicity (aliphatic chain/ring, aromatic ring) | Aromatic ring dummy | Halogen | Hydrogen-bonding donor | Hydrogen-bonding acceptor | Hydrogen-bonding donor/ acceptor |
|---|---|---|---|---|---|---|
| Hydrophobicity (aliphatic chain/ring, aromatic ring) | +3 | 0 | (+3) | −2 | −2 | −2 |
| Aromatic ring dummy | 0 | +1 | 0 | 0 | 0 | 0 |
| Hydrophobicity (halogen) | (+3) | 0 | (+3) | (−2) | (−2) | (−2) |
| Hydrogen-bonding donor | −2 | 0 | (−2) | +2 | −2 | +1 |
| Hydrogen-bonding acceptor | −2 | 0 | (−2) | −2 | +2 | +1 |
| Hydrogen-bonding donor/ acceptor | −2 | 0 | (−2) | +1 | +1 | +1 |

(1) the characteristic groups (atoms) of compounds are roughly divided into four types of hydrophobicity (aliphatic chain/ring, aromatic ring and halogen), hydrogen-bonding donor, hydrogen-bonding acceptor and hydrogen-bonding donor/acceptor,
(2) a molecule of compound with large radius of inertia calculated from constituting characteristic groups (atoms) is fixed, superposition is performed among a set of distinctive characteristic groups (atoms), and operations of translation and rotation are performed in its neighborhood,
(3) when causing the superposition of characteristic groups (atoms) between molecules of compounds by the operations of translation and rotation in (2), a score is given depending on the combination between respective characteristic groups (atoms), and
(4) scores of superposition are summed up.

The invention is a novel method (algorithm) for superposing the molecular structures of compounds for drugs, agricultural chemicals, etc., and it can be applied in the process of presuming active conformations from a number of metastable structures. Since the inventive superposing method (algorithm) is very rapid, it can be utilized for the creation of lead compounds for drugs, agricultural chemicals, etc. based on the presumption of active conformations and the three-dimensional structure database searching.

The process of superposition is described in FIG. 1. In following, each step will be explained. The characteristic groups (atoms) of compounds are roughly divided into four types of hydrophobicity (aliphatic chain/ring, aromatic ring and halogen), hydrogen-bonding donor, hydrogen-bonding acceptor and hydrogen-bonding donor/acceptor, and score is Here, the absolute values of figures in Table are exemplified and not fixed.

Since the atomic position of each ligand molecule is not necessarily coincide for binding to proteins such as receptor and enzyme, each characteristic group (atom) is approximated with a sphere, and, if two spheres are overlapped even a little, they are added to score. The radii of the spheres of characteristic groups (atoms) are considered to be different in size between resonance system and others, and, for example, it is possible to put the resonance system on 0.05 nanometers and others on 0.1 nanometer.

Each characteristic group (atom) that constitutes the molecule is allotted based on, for example, following rules.
1. On oxygen atom of carbonyl, sulfone, phospho, ester, ether, etc., a sphere of hydrogen-bonding acceptor can be placed.
a) With oxygen atom of $CO_2^-$, $SO_2$, $PO_2^-$, etc., the radius of a sphere of hydrogen-bonding acceptor is 0.05 nanometers.
b) In a), it is also possible to place a sphere of hydrogen-bonding acceptor with radius of 0.1 nanometer in the middle point of two oxygen atoms.
2. On oxygen atom of hydroxyl group and sulfur atom of thiol, a sphere of hydrogen-bonding donor/acceptor with radius of 0.1 nanometer can be placed.
3. On nitrogen atom of amine, amide, amidine, guanidine, etc. that accompanies with hydrogen atom, a sphere of hydrogen-bonding donor can be placed.
a) With nitrogen atom of amidine, guanidine, etc., the radius of a sphere of hydrogen-bonding donor is 0.05 nanometers.
b) In a), it is also possible to place a sphere of hydrogen-bonding donor with radius of 0.1 nanometer in the middle point of two nitrogen atoms.

4. Aromatic ring of phenyl, naphthalene, pyridine, thiophene, etc. is hydrophobic, and it is possible to place a sphere of hydrophobicity (aromatic ring) with radius of 0.1 nanometer in the center of ring.
5. Aliphatic chain (including branch) of alkyl, thioether, etc. with chain length of 3 or more is hydrophobic (aliphatic chain/ring).
a) On branched carbon atom, a sphere of hydrophobicity (aliphatic chain/ring) with radius of 0.1 nanometer can be placed.
b) On carbon atom at the third position counting from the position of the root of main chain (the atom at the root is not allotted as a characteristic group (atom), otherwise counting is made from the next atom), a sphere of hydrophobicity (aliphatic chain/ring) with radius of 0.1 nanometer can be placed.
c) On the position adjacent to characteristic group (atom) being hydrogen-bonding donor, hydrogen-bonding acceptor and hydrogen-bonding donor/acceptor, a sphere of hydrophobicity (aliphatic chain/ring) cannot be placed.
d) Spheres of hydrophobicity (aliphatic chain/ring) cannot be placed continuously (two atoms should be interposed).
e) With piperidine and pyrrolidine, it is possible to place a sphere of hydrophobicity (aliphatic chain/ring) with radius of 0.1 nanometer in the center of ring.
6. Trifluoromethyl group is hydrophobic, and it is possible to place a sphere of hydrophobicity (aliphatic chain/ring) with radius of 0.1 nanometer on the central carbon atom.

For performing the superposition of the molecular structures of compounds, at first, their coordinates are converted to average coordinates (aromatic ring dummy is not included) calculated from characteristic groups (atoms) constituting each molecule. And, a molecule with large radius of inertia (aromatic ring dummy is not included) calculated from those characteristic groups (atoms) is fixed and small molecule is rotated and translated. The rotation is performed making the origin of coordinates of molecule as a center. The ranges are made to be $0 \leq \phi, \psi < 360°, 0 \leq \theta \leq 180°$, using three Eulerian angles, and the incremental angle (°) is determined from the number of increments of the circumference that makes the maximum value of distance from the origin to a characteristic group (atom) as a radius, divided by the diameter of that characteristic group (atom). Actually, the incremental angles are calculated from the characteristic groups (atoms) with radius of 0.1 nanometer and with radius of 0.05 nanometers that are most away from the origin each, and the smaller incremental angle is adopted. The translation is implemented in all combinations that make the score values of superpositions between characteristic groups (atoms) positive. Ordinarily, this is performed on the position of each characteristic group (atom) of the fixed molecule and eight cubic vertexes around it. If need be, the translation is possible also on additional six face-centered points. In the case of the radius of characteristic group (atom) being 0.05 nanometers, this is, for example, on the points of body-centered cubic lattice with a side 0.1 nanometer long, and, in the case of the radius of characteristic group (atom) being 0.1 nanometer, this is, for example, on the points of body-centered cubic lattice with a side 0.15 nanometers long. Besides, when the characteristic functional groups concerned in the activity can be presumed from the knowledge on structure-activity relationships, and the like, it is not needed to perform the translating operation based on all combinations of characteristic groups (atoms) with the same nature, it is only necessary to make only the translating operation between particular characteristic groups (atoms) as target.

The score value to be added by the superposition between characteristic groups (atoms) is determined by the combinations thereof. With respect to the aromatic ring, if placing a sphere of hydrophobicity (aromatic ring) with radius of 0.1 nanometer in the center of ring, dummy spheres with radius of 0.05 nanometers are added automatically at upper and lower positions away from 0.19 nanometers. In the superposition between aromatic rings, when all of one sphere of hydrophobicity (aromatic ring) and two dummy spheres are superposed, 4 points are added and, when one sphere of hydrophobicity (aromatic ring) is superposed, 3 points are added.

Score is calculated on the orientations of all of said superpositions, respectively, and an orientation with the highest value is adopted. If the highest value of score is redundant, then one with smaller rmsd (root-mean-square deviation, nanometer) in the distance between superposed characteristic groups (atoms) is selected. For the calculation of rmsd, however, the superpositions of more than one pair of characteristic groups (atoms) are also taken into consideration (aromatic dummy is not taken into consideration). Thereafter, for further improving the score, the translation and rotation are adjusted slightly by simplex method, using rmsd as an objective function to determine the final orientation of superposition.

Best embodiment to put the invention into practice

The superpositions of enzyme inhibitors were performed to compare with the superpositions obtained from the X-ray crystallography of enzyme-inhibitor complexes. The superposition of enzyme inhibitors was performed using three-dimensional coordinates registered in protein data bank (PDB, Brookhaven Protein Data Bank). The abbreviated name of inhibitors and the registration code in bracket are as described in PDB.

EXAMPLE 1
HIV-1 Protease Inhibitors
A-74704 (9HVP) & MVT-101 (4HVP)

EXAMPLE 2
Thrombin Inhibitors
NAPAP (1ETS) & MQPA (1ETR)

EXAMPLE 3
Thrombin Inhibitors
MQPA (1ETR) & 4-TAPAP (1ETT)

EXAMPLE 4
Trypsin Inhibitors
PRA (1TNK) & AMC (1TNG)

EXAMPLE 5
Trypsin Inhibitors
PRA (1TNK) & BEN (2TBS)

EXAMPLE 6
Carboxypeptidase A Inhibitors
FVF (7CPA) & BZS (1CBX)

EXAMPLE 7
Carboxypeptidase A Inhibitors
FVF (7CPA) & AGF (8CPA)

EXAMPLE 8
Elastase Inhibitors
BDK (1EAU) & TFK (1EAS)

EXAMPLE 9
Elastase Inhibitors
TFA-Lys-Ala-ANI (2EST) & TFA-Leu-Ala-ANI (7EST)

EXAMPLE 10
Elastase Inhibitors
TFK (1EAS) & TFA-Lys-Leu-ISO (1ELB)

EXAMPLE 11
Elastase Inhibitors
12 Residues of OMTKY3 (1PPF) & Ace-Ala-Pro-Val-FPA (4EST)

EXAMPLE 12
Thermolysin Inhibitors
CBZ-PGL-Leu-Leu (5TMN) & PHO-Leu-NH$_2$ (2TMN)
Abbreviated Name of Inhibitors
A-74704: (2S,4S)-2,4-bis-((N-(N-carbobenzyloxy)-valyl)amino)-1,5-diphenyl-3-hydroxypentane
MVT-101: N-acetyl-L-threonyl-L-isoleucyl-L-norleucyl-ψ-(methyleneamino)-L-norleucyl-L-glutaminyl-L-argininamide
NAPAP: Nα-(2-naphthyl-sulfonyl-glycyl)-DL-p-amidinophenylalanyl-piperidine
MQPA: (2R,4R)-4-methyl-1-[Nα-(3-methyl-1,2,3,4-tetrahydro-8-quinolinesulfonyl)-L-arginyl]-2-piperidine carboxylic acid
4-TAPAP: Nα-(4-toluene-sulfonyl)-DL-p-amidinophenylalanyl-piperidine
PRA: 3-Phenylpropylamine
AMC: Aminomethylcyclohexane
BEN: Benzamidine
FVF: O-[[(1R)-[[N-(phenylmethoxycarbonyl)-L-phenylalanyl]-amino]isobutyl]hydroxyphosphinyl]-L-3-phenyllactate
BZS: L-Benzylsuccinate
AGF: O-[[(1R)-[[N-(phenylmethoxycarbonyl)-L-alanyl]amino]-methyl]hydroxyphosphinyl]-L-3-phenyllactate
BDK: 2-[5-Amino-6-oxo-2-(2-thienyl)-1,6-dihydropyrimidine-1-yl]-N-[3,3-difluoro-1-isopropyl-2-oxo-3-[N-(2-morpholino-ethyl)carbamoyl]propyl]acetamide
TFK: 3-[[(Methylamino)sulfonyl]amino]-2-oxo-6-phenyl-N-[3,3,3-trifluoro-1-(1-methylethyl)-2-oxopropyl]-1(2H)-pyridineacetamide
TFA-Lys-Ala-ANI: Trifluoroacetyl-L-lysyl-L-alanyl-p-trifluoromethylphenylanilide
TFA-Leu-Ala-ANI: Trifluoroacetyl-L-leucyl-L-alanyl-p-trifluoromethylphenylanilide
TFA-Lys-Leu-ISO: Trifluoroacetyl-L-lysyl-L-leucyl-p-isopropylanilide
OMTKY3: The third domain of turkey ovomucoid inhibitor
Ace-Ala-Pro-Val-FPA: Acetyl-L-alanyl-L-propyl-L-valyl-difluoro-N-phenylethylacetamide
CBZ-PGL-Leu-Leu: Carbobenzoxy-glycyl$^P$-L-leucyl-L-leucine (glycyl$^P$ is used to indicate that the trigonal carbon of the peptide linkage is replaced by the tetrahedral phosphorus of a phosphonamidate group.)
PHO-Leu-NH$_2$: N-Phosphoryl-L-leucinamide

TABLE 2

Results of superposition

| Example | Inhibitor | Score | rmsd | Incremental Angle |
|---|---|---|---|---|
| 1 | A74704 & MVT-101 | 29 | 1.5 | 2 |
| 2 | NAPAP & MQPA | 24 | 1.3 | 5 |
| 3 | MQPA & 4-TAPAP | 23 | 1.2 | 5 |
| 4 | PRA & AMC | 6 | 1.3 | 13 |
| 5 | PRA & BEN | 6 | 1.2 | 13 |
| 6 | FVF & BZS | 12 | 0.3 | 7 |
| 7 | FVF & AGF | 28 | 0.5 | 4 |
| 8 | BDK & TFK | 21 | 0.4 | 4 |
| 9 | TFA-Lys-Ala-ANI & TFA-Leu-Ala-ANI | 25 | 0.4 | 5 |
| 10 | TFK & TFA-Lys-Leu-ISO | 17 | 1.6 | 5 |
| 11 | Part of OMTKY3 & Ace-Ala-Pro-Val-FPA | 21 | 1.5 | 3 |
| 12 | CBZ-PGL-Leu-Leu & PHO-Leu-NH$_2$ | 13 | 0.4 | 8 |

Figure 3:
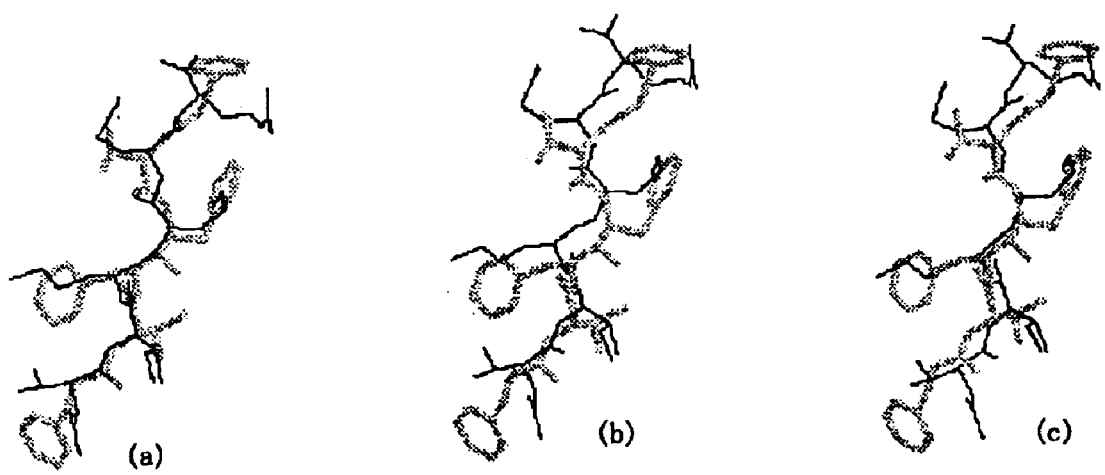
FIG. 3 shows the superpositioning of molecular structures of the Examples.
Figure 5:
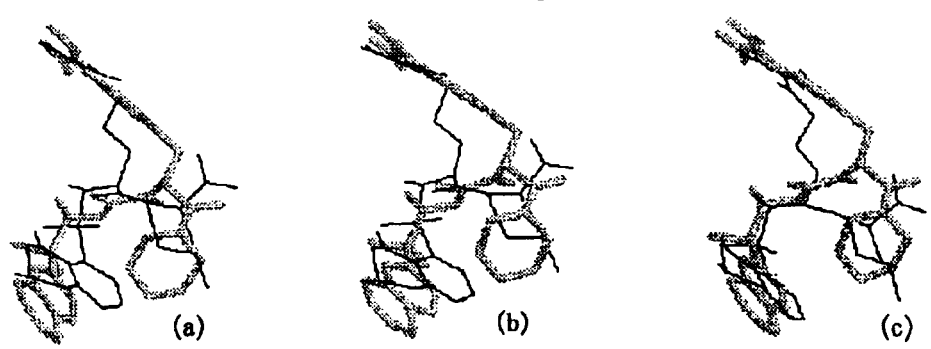
FIG. 5 shows the results of an Example including superpositioning of molecular structures.

The results of Examples 1 and 2 are described in FIG. 3 and FIG. 5. In the diagrams, left side shows the superposition obtained from X-ray crystallography, middle shows the superposition obtained by the invention method without an anchor, and right side shows the superposition obtained by the invention method with an anchor. All the superpositions of enzyme inhibitors in the examples reproduced the superpositions obtained from X-ray crystallography. Furthermore, the use of anchors made these superpositions more than several tens times (a hundred times) as high speed as before, which was practical.

(FIG. 1)
An illustration diagram showing the processes (a), (b), (c), (d), (e) and (f) of superposition according to the invention.

(a) is a process for the input of three-dimensional co-ordinates of molecule of compound and the designation of characteristic groups (atoms) which are roughly divided into four types of hydrophobicity, hydrogen-bonding donor, hydrogen-bonding acceptor and hydrogen-bonding donor/acceptor.

(b) is a process for translating the gravity center of molecule of compound to the origin of-coordinates.

(c) is a process for the rotation ($0°≦\phi$, $\psi<360°$, $0°≦\theta≦180°$) of molecule of compound with small radius of inertia.

(d) is a process for the translation (onto body-centered cubic lattice points or face-centered cubic lattice points of characteristic groups (atoms) of the counter molecule) of molecule of compound with small radius of inertia.

(c) and (d) are repeated again and again.

(e) is a process for determining the best superposition. Criterion of evaluation (order of priority)
1) Highest score value, 2) Minimum value of rmsd (f) is a process for optimizing the superposition by simplex method.

(FIG. 2)
An illustration diagram showing the structural formulae of inhibitors in Example 1.
(a) shows the structural formula of A-74704, and
(b) shows the structural formula of MVT-101.

(FIG. 3)
An illustration diagram showing the results of Example 1.
(a) shows the superposition of molecular structures obtained from X-ray crystallography,
(b) shows the superposition of molecular structures obtained by the inventive method without an anchor, and
(c) shows the superposition of molecular structures obtained by the inventive method with an anchor, respectively.

(FIG. 4)

An illustration diagram showing the structural formulae of inhibitors in Example 2.
(a) shows the structural formula of MQPA, and
(b) shows the structural formula of NAPAP
(FIG. 5)
An illustration diagram showing the results of Example 2.
(a) shows the superposition of molecular structures obtained from X-ray crystallography,
(b) shows the superposition of molecular structures obtained by the inventive method without an anchor, and
(c) shows the superposition of molecular structures obtained by the inventive method with an anchor, respectively.

Figure 4:
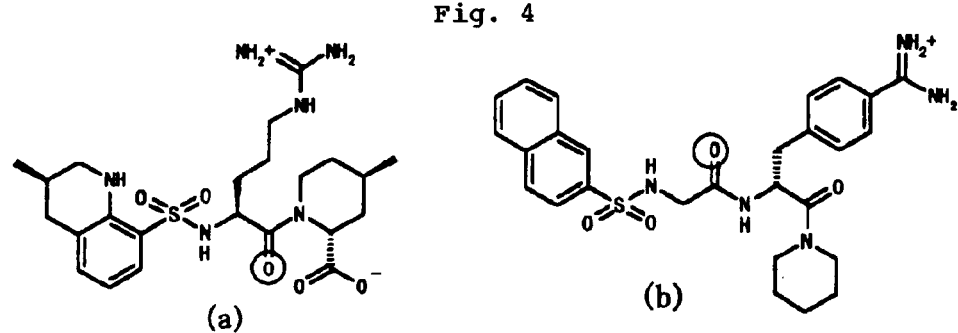
FIG. 4 shows a structural formula for an inhibitor of the Examples.

Explanation of the Symbol
○ in FIG. 2 indicates an anchor.
Bold line in FIG. 3 indicates A-74704.
Fine line in FIG. 3 indicates MVT-101.
○ in FIG. 4 indicates an anchor.
Bold line in FIG. 5 indicates NAPAP.
Fine line in FIG. 5 indicates MQPA.

What is claimed is:

1. A method for superposing molecular structures of a plurality of compounds comprising a plurality of characteristic groups, said method comprising:
   (i) dividing said plurality of characteristic groups of said plurality of compounds into four types selected from
   a hydrophobic group, which comprises aliphatic chain/ring group, aromatic ring group, a halogen group, and mixtures thereof, wherein one or more aromatic ring dummies are placed at upper and lower positions away from said aromatic ring,
   a hydrogen-bonding donor group,
   a hydrogen-bonding acceptor group, and
   a hydrogen-bonding donor/acceptor group;
   (ii) fixing a molecule of a first compound from said plurality of compounds having a large radius of inertia calculated from said plurality of characteristic groups;
   (iii) performing superposition among a set of characteristic groups with the same nature between said first compound and a second compound from said plurality of compounds to obtain superposed groups by carrying out operations of translation and rotation in the neighborhood of said first compound;
   (iv) assigning scores to said set of characteristic groups present in said superposed groups;
   (v) summing up said scores of said superposed groups.

2. The method according to claim 1, wherein said operations of translation further comprises a face-centering translation.

3. The method according to claim 1, wherein said operations of translation further comprises a body-centering translation.

4. The method according to claim 2, wherein said operations of translation further comprises a body-centering translation.

5. The method according to claim 1, further comprising after the first step:
   selecting a characteristic group from each of said first and second compound and constraining said characteristic group from each of said first and second compound.

6. The method according to claim 1, further comprising:
   (vi) repeating said operations of (ii) through (v) to find an orientation that acquires the highest score value.

7. The method according to claim 6, wherein said operations of translation further comprises a face-centering translation.

8. The method according to claim 7, wherein said operations of translation further comprises a body-centering translation.

9. The method according to claim 6, wherein said operations of translation further comprises a body-centering translation.

10. A method for superposing molecular structures of a plurality of compounds comprising a plurality of characteristic groups, said method comprising:
    (i) dividing said plurality of characteristic groups of said plurality of compounds into four types selected from
    a hydrophobic group, which comprises aliphatic chain/ring group, aromatic ring group, halogen group, or mixtures thereof,
    a hydrogen-bonding donor group,
    a hydrogen-bonding acceptor group, and
    a hydrogen-bonding donor/acceptor group;
    (ii) fixing a molecule of a first compound from said plurality of compounds having a large radius of inertia calculated from said plurality of characteristic groups;
    (iii) performing superposition among a set of characteristic groups with the same nature between said first compound and a second compound from said plurality of compounds to obtain superposed groups by carrying out operations of translation and rotation in the neighborhood of said first compound, wherein said translation comprises a face-centering translation;
    (iv) assigning scores to said set of characteristic groups present in said superposed groups;
    (v) summing up said scores of said superposed groups.

11. The method according to claim 10, wherein said operations of translation further comprises a body-centering translation.

12. The method according to claim 10, further comprising after the step (i):
    selecting a characteristic group from each of said first and second compound and constraining said characteristic group from each of said first and second compound.

13. The method according to claim 10, further comprising:
    (vi) repeating said operations of (ii) through (v) to find an orientation that acquires the highest score value.

14. The method according to claim 13, wherein said operations of translation further comprises a body-centering translation.

15. A method for superposing one or more molecular structures of one or more compounds comprising one or more characteristic groups, said method comprising:
    (i) dividing the characteristic groups into one or more groups selected from the group consisting of a hydrophobic group, a hydrogen-bonding donor group, a hydrogen-bonding acceptor group and a hydrogen-bonding donor/acceptor group;
    (ii) fixing a first molecule of the compound, wherein the first molecule has the largest radius of inertia calculated from the characteristic groups of the molecule;
    (iii) superpositioning the characteristic groups between at least the first molecule and a second molecule of the compounds by translating and rotating the characteristic groups of the second molecule around the first molecule;
    (iv) assigning a score to the translating and rotating, wherein the score is based on the combination of characteristic groups between the first and second molecules;

(v) summing the scores of the superpositioning; and (vi) repeating the fixing, superpositioning, assigning and summing to determine an 16. The method of claim 15, wherein the divided characteristic groups include at least one hydrophobic group selected from the group consisting of an aliphatic chain/ring, an aromatic ring and a halogen orientation having the highest score value.

17. The method of claim 15, wherein the molecule having the largest radius of inertia has a volume smaller than the molecule translated and rotated around the compound with the largest radius of inertia.

18. A method for superposing one or more molecular structures of one or more compounds comprising one or more characteristic groups, wherein the molecular structures are superposed onto one or more compounds having an active characteristic functional group, (i) dividing the characteristic groups into one or more groups selected from the group consisting of a hydrophobic group, a hydrogen-bonding donor group, a hydrogen-bonding acceptor group and a hydrogen-bonding donor/acceptor group;

(ii) fixing a first molecule of the compound, wherein the first molecule has the largest radius of inertia calculated from the characteristic groups of the molecule;

(iii) superpositioning the characteristic groups between at least the first molecule and a second molecule of the compounds by translating and rotating the characteristic groups of the second molecule around the first molecule;

(iv) assigning a score to the translating and rotating, wherein the score is based on the combination of characteristic groups between the first and second molecules; and (v) summing the scores of the superpositioning.

19. The method of claim 18, wherein the divided characteristic groups include at least one hydrophobic group selected from the group consisting of an aliphatic chain/ring, an aromatic ring and a halogen.

20. The method of claim 18, wherein the molecule having the largest radius of inertia has a volume smaller than the molecules translated and rotated around the compound with the largest radius of inertia.

21. A method for superposing molecular structures of a plurality of compounds comprising a plurality of characteristic groups, said method comprising:

(i) dividing said plurality of characteristic groups of said plurality of compounds into four types selected from the group consisting of a hydrophobic group selected from the group consisting of an aliphatic chain/ring group, aromatic ring group, a halogen group, and mixtures thereof, wherein two aromatic ring dummies are placed at upper and lower positions away from the center of the aromatic ring group when an aromatic ring group is present, a hydrogen-bonding donor group, a hydrogen-bonding acceptor group, and a hydrogen-bonding donor/acceptor group;

(ii) representing each characteristic group as a property sphere;

(iii) fixing the spheres representing a first compound structure having the largest radius of diameter;

(iv) selecting a property sphere out of the spheres representing the first compound structure;

(v) selecting a property sphere out of the spheres representing a second compound structure having a radius of inertia smaller than the radius of inertia of the first compound structure to be a set of characteristics groups with the same nature between the first and second compound structures;

(vi) performing superposition of the spheres between the first compound structure and the second compound structure by superposing a set of selected property spheres;

(vii) generating at least one of a plurality of body-centered lattice points or face-centered cubic lattice points around the selected property sphere in the first compound structure;

(viii) performing translation of the property spheres representing the second compound structure by superposing the selected property sphere in the second compound structure onto the selected property sphere and the lattice points around the property sphere in the first compound structure;

(ix) assigning scores to the superposed property spheres;

(x) summing up said scores of said superposed property spheres;

(xi) rotating the spheres representing the second compound structure based on the origin calculated by averaging the property sphere coordinates of the second compound structure;

(xii) repeating (iv) through (xi) to find an orientation that acquires the highest score value.

* * * * *